United States Patent
Ouchi et al.

(10) Patent No.: US 11,291,805 B2
(45) Date of Patent: Apr. 5, 2022

(54) MEDICAL ELONGATED BODY AND MEDICAL ELONGATED BODY SET

(71) Applicant: TERUMO KABUSHIKI KAISHA, Tokyo (JP)

(72) Inventors: Tatsuya Ouchi, Shizuoka (JP); Ryo Okamura, Fujinomiya (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 104 days.

(21) Appl. No.: 16/519,723

(22) Filed: Jul. 23, 2019

(65) Prior Publication Data
US 2019/0344051 A1    Nov. 14, 2019

Related U.S. Application Data (63) Continuation of application No. PCT/JP2018/004439, filed on Feb. 8, 2018.

(51) Int. Cl.
*A61M 25/06* (2006.01)
*A61M 25/01* (2006.01)
(Continued)

(52) U.S. Cl.
CPC .... *A61M 25/0662* (2013.01); *A61M 25/0138* (2013.01); *A61M 25/04* (2013.01);
(Continued)

(58) Field of Classification Search
CPC .......... A61M 25/0662; A61M 25/0138; A61M 25/04; A61M 2025/0059;
(Continued)

(56) References Cited

U.S. PATENT DOCUMENTS

| 2003/0233083 A1 | 12/2003 | Houwaert et al. |
| 2008/0039823 A1 | 2/2008 | Shimogami et al. |

(Continued)

FOREIGN PATENT DOCUMENTS

| CN | 1658814 A | 8/2005 |
| CN | 101020093 A | 8/2007 |

(Continued)

OTHER PUBLICATIONS

Office Action (The First Office Action) dated Apr. 26, 2021, by the State Intellectual Property Office of People's Republic of China in corresponding Chinese Patent Application No. 201880004287.1 and an English Translation of the Office Action. (17 pages).

(Continued)

*Primary Examiner* — Amber R Stiles
(74) *Attorney, Agent, or Firm* — Buchanan Ingersoll & Rooney PC (57) ABSTRACT

A medical elongated body and a medical elongated body set are constructed in a way that expedites medical instrument insertion into a tubular body lumen via a valve body. The medical elongated body includes a tubular body insertable into a body lumen, a hub having an internal space communicating with a lumen of the tubular body and disposed in a proximal portion of the tubular body, a valve body disposed in the internal space and having an insertion portion, and a cap member that fixes the valve body in the internal space by being attached to the valve body and has a proximal opening portion to communicate with the internal space via the insertion portion. The cap member has a marker portion that guides a medical instrument inserted into the tubular body to the valve body. The marker portion has a color distinguishable from a periphery of the marker portion.

22 Claims, 6 Drawing Sheets

(51) Int. Cl.
*A61M 25/04* (2006.01)
*A61M 25/00* (2006.01)
*A61M 25/02* (2006.01)

(52) U.S. Cl.
CPC ............... *A61M 2025/0059* (2013.01); *A61M 2025/0246* (2013.01); *A61M 2025/0293* (2013.01); *A61M 2025/0681* (2013.01)

(58) Field of Classification Search
CPC .. A61M 2025/0246; A61M 2025/0293; A61M 2025/0681; A61M 29/00; A61M 39/06; A61M 2039/062; A61M 2039/0626; A61M 2039/0633; A61M 2039/066
See application file for complete search history.

(56) References Cited

U.S. PATENT DOCUMENTS

| | | | |
|---|---|---|---|
| 2013/0158519 A1 | 6/2013 | Boutilette et al. | |
| 2014/0114286 A1* | 4/2014 | Okamura | A61M 25/0097 604/523 |
| 2014/0276037 A1 | 9/2014 | Johnson et al. | |

FOREIGN PATENT DOCUMENTS

| | | |
|---|---|---|
| CN | 103619399 A | 3/2014 |
| CN | 105073022 A | 11/2015 |
| JP | 2009189861 A | 8/2009 |
| JP | 2013208428 A | 10/2013 |
| JP | 2016215026 A | 12/2016 |

OTHER PUBLICATIONS

An English Translation of the International Search Report (Form PCT/ISA/210) and the Written Opinion of the International Searching Authority (Form PCT/ISA/237) dated May 1, 2018, by the Japanese Patent Office in corresponding International Application No. PCT/JP2018/004439. (9 pages).

International Search Report (PCT/ISA/210) dated May 1, 2018, by the Japanese Patent Office as the International Searching Authority for International Application No. PCT/JP2018/004439.

Written Opinion (PCT/ISA/237) dated May 1, 2018, by the Japanese Patent Office as the International Searching Authority for International Application No. PCT/JP2018/004439.

* cited by examiner

MEDICAL ELONGATED BODY AND MEDICAL ELONGATED BODY SET

CROSS-REFERENCES TO RELATED APPLICATIONS

This application is a continuation of International Application No. PCT/JP2018/004439 filed on Feb. 8, 2018, an claims priority to Japanese Application No. 2017-023529 filed on Feb. 10, 2017, the entire content of both of which is incorporated herein by reference.

TECHNICAL FIELD

The present invention generally relates to a medical elongated body and a medical elongated body set each having a tubular body insertable into a body lumen.

BACKGROUND DISCUSSION

In the medical field, a medical elongated body having a tubular body insertable into a body lumen is used when medical devices such as various catheters are percutaneously introduced into a living body. The medical elongated body is, for example, an introducer sheath including a tubular body insertable into a body lumen, a hub disposed in the proximal portion of the tubular body, and a valve body disposed in the hub.

The introducer sheath is percutaneously introduced into the body lumen from the distal side of the tubular body so that an access path connecting the inside of a living body and the outside of the living body is formed. A dilator (medical instrument) is inserted into the lumen of the introducer sheath at this time so that the rigidity of the tubular body is enhanced. In addition, a medical instrument such as a guide wire and a catheter is inserted into the introducer sheath in a state where the distal side of the tubular body is in the body lumen and the proximal side of the tubular body is exposed to the outside of the living body (in a state where the access path connecting the inside of the living body and the outside of the living body is formed).

As described above, an operator such as a doctor inserts a medical instrument into the lumen of the tubular body via the valve body disposed in the tubular body in using the introducer sheath. At this time, the operator needs to pay attention such that the distal portion of the medical instrument is near the center of the valve body so that, for example, damage to the medical instrument attributable to contact between the distal portion of the medical instrument and a place other than the valve body is prevented. This is an obstacle to expediting medical instrument insertion into the tubular body lumen via the valve body. Japanese Patent Application Publication No. 2013-208428 discloses a medical elongated body including, for example, a device for guiding a medical instrument to a valve body.

SUMMARY

In the case of the medical elongated body, the number of parts increases by the amount of the device and the structure of the medical elongated body as a whole becomes complicated. Problems arise as a result, including an increase in medical elongated body manufacturing cost.

The medical elongated body and medical elongated body set disclosed here have a relatively simple structure capable of expediting medical instrument insertion into a tubular body lumen via a valve body.

A medical elongated body comprises a tubular body insertable into a body lumen of a patient, wherein the tubular body includes a lumen; a hub that includes an internal space communicating with the lumen of the tubular body and disposed in a proximal portion of the tubular body; a valve body disposed in the internal space of the hub and including an insertion portion through which is insertable a medical instrument when the tubular body is positioned in the body lumen of the patient to introduce the medical instrument into the body lumen of the patient; and a cap member attached to the valve body in a manner fixing the valve body in the internal space of the hub. The cap member includes a proximal opening portion configured to communicate with the internal space via the insertion portion. The cap member also includes a marker portion that guides the medical instrument to the valve body during insertion of the medical instrument into the tubular body, and the marker portion is of a color that is visually distinguishable from a periphery of the marker portion According to another aspect, a medical elongated body comprises a tubular body insertable into a body lumen of a patient, with the tubular body including a lumen; a hub that includes an internal space communicating with the lumen of the tubular body and disposed in a proximal portion of the tubular body; a valve body disposed in the internal space of the hub and including an insertion portion through which is insertable a medical instrument when the tubular body is positioned in the body lumen of the patient to introduce the medical instrument into the body lumen of the patient; and a cap member attached to the valve body in a manner fixing the valve body in the internal space of the hub. The cap member includes a proximal opening portion configured to communicate with the internal space via the insertion portion. The valve body including a marker portion that guides the medical instrument to the insertion portion during insertion of the medical instrument into the tubular body, and the marker portion is of a color that is visually distinguishable from a periphery of the marker portion A medical elongated body set for achieving the above-described object includes the medical elongated body and a dilator insertable into a lumen of the medical elongated body. The medical elongated body is an introducer sheath, and a distal end marker portion is of a color distinguishable from a surrounding is provided in a distal portion of the dilator.

According to another aspect, a medical elongated body comprises: a tubular body possessing a lumen into which a medical instrument is insertable, with the tubular body possessing a proximal portion; a hub connected to the proximal portion of the tubular body, with the hub possessing an internal space communicating with the lumen of the tubular body and also possessing an inner surface and a proximal portion. A valve body is disposed in the proximal portion of the hub and covers the internal space so that the internal space is bounded by the valve body and the inner surface of the hub, with the valve body possessing a center and including an insertion portion into which a medical instrument is insertable, and the valve body possessing a proximal surface facing away from the tubular body and a distal surface facing toward the tubular body. The valve body includes a proximal surface and a distal surface positioned on opposite surfaces of the valve body, and a cap member is attached to the proximal portion of the hub and is in direct contact with the proximal surface of the valve body. The cap member possesses a centrally located proximal opening portion passing through the cap member. The insertion portion is exposed in the proximal opening portion of the cap member so that the medical instrument is insertable into the insertion portion of the valve body while passing through the proximal opening portion of the cap member. The cap member includes a marker portion that guides the medical instrument to the insertion portion of the valve body during insertion of the medical instrument into the tubular body. The insertion portion includes a proximal side slit located on the proximal surface of the valve body and a distal side slit located on the distal surface of the valve body, with the proximal side slit including oppositely disposed end portions, and with the distal side slit intersecting the proximal end slit. The cap member is in direct contact with the proximal surface of the valve body at a position that is closer to the center of the valve body than both end portions of the proximal side slit of the valve body, and the marker portion is disposed at a position surrounding the proximal side slit while covering both end portions of the proximal side slit.

With the medical elongated body and the medical elongated body set disclosed here, an operator can easily grasp the position of a hemostatic valve by visually recognizing the marker portion during insertion of a medical instrument into the tubular body lumen via the valve body. Accordingly, the operator can easily guide the distal portion of the medical instrument to the vicinity of the center of the hemostatic valve by aiming at the position indicated by the marker portion. Accordingly, it is possible to provide a medical elongated body and a medical elongated body set each having a simple structure that allows quick insertion of a medical instrument into a tubular body lumen via a valve body.

DETAILED DESCRIPTION

Embodiment 1

Set forth below with reference to the accompanying drawings is a detailed description of embodiments of an introducer set 10 representing examples of the inventive introducer set disclosed here.

FIGS. 1 to 4 are diagrams illustrating each portion of the introducer set 10.

Figure 1:
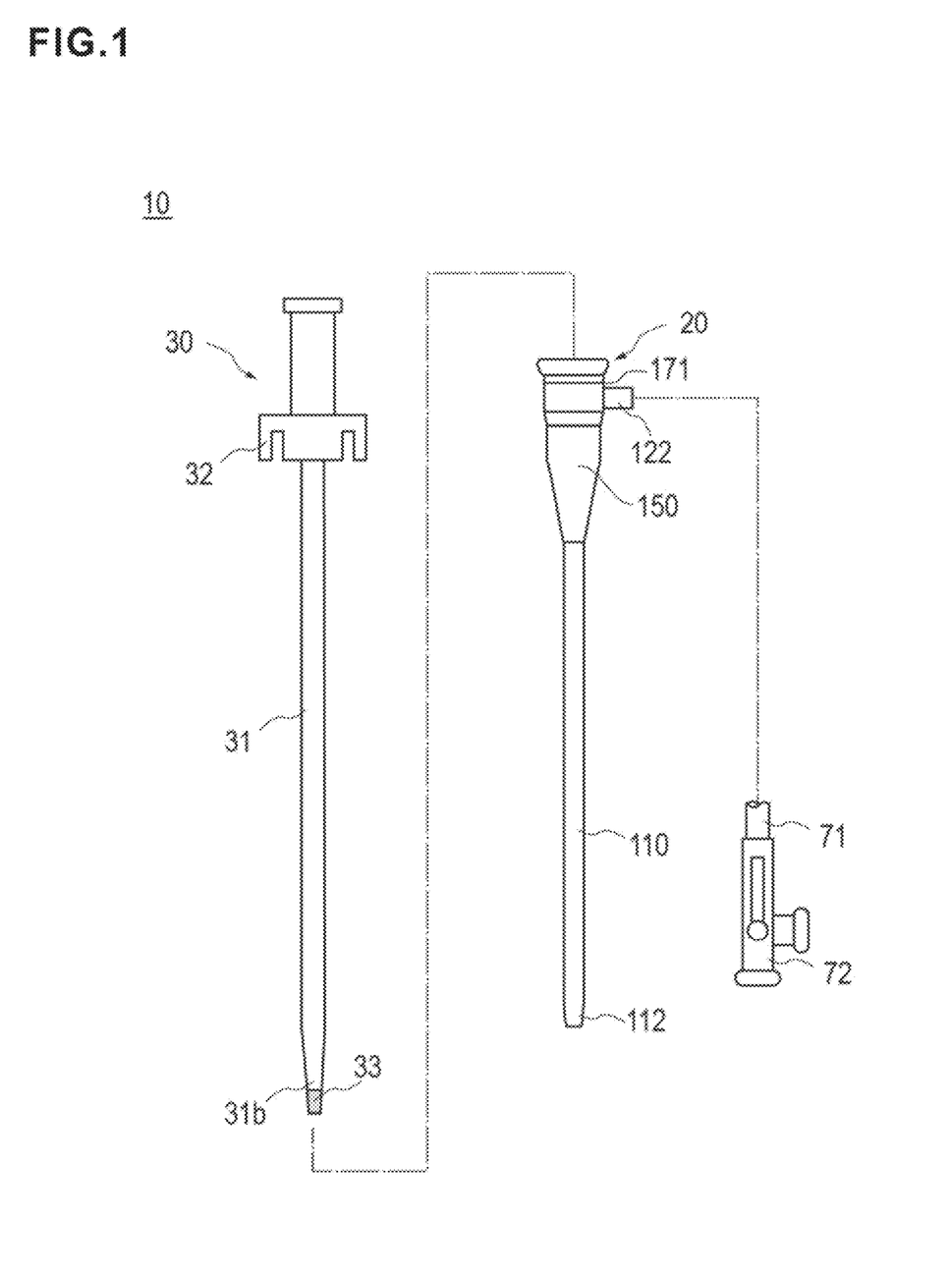
FIG. 1 is a diagram illustrating an introducer set according to Embodiment 1.
Figure 3:
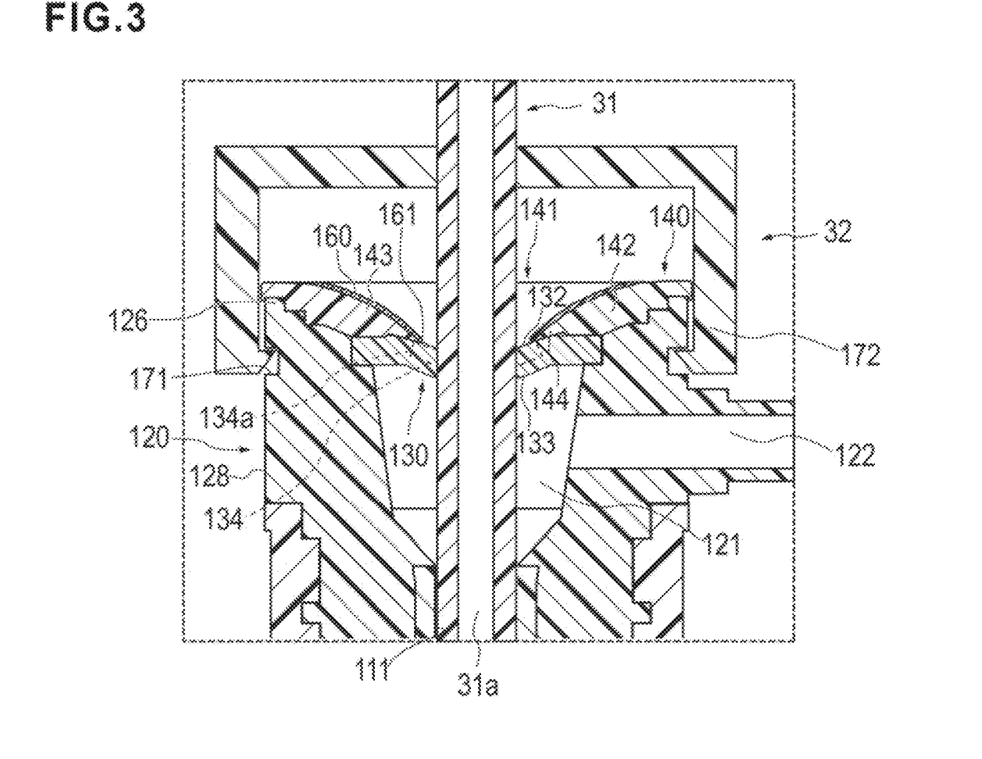
FIG. 3 is an enlarged view of Dashed Line Portion 3 in FIG. 2.

Referring to FIGS. 1 and 3, the introducer set 10 that is in a state where a dilator 30 is inserted in a catheter main body 110 of an introducer sheath 20 is referred to as an introducer assembly in this specification. In the introducer assembly, the side on which a hub 120 of the introducer sheath 20 and a dilator hub 32 of the dilator 30 are disposed (upper side in FIG. 1) is referred to as the "proximal side" (proximal end). In the introducer assembly, the side that is located on the side opposite to the proximal side and is introduced into a body lumen (lower side in FIG. 1) is referred to as "distal side" (distal end). The direction in which the introducer sheath 20 and the dilator 30 extend (up-down direction in FIG. 1) is referred to as "axial direction". "Distal portion" means a certain range including the distal end (the most distal end) and the periphery of the distal end (the most distal end) and "proximal portion" means a certain range including the proximal end (the most proximal end) and the periphery of the proximal end (the most proximal end).

As illustrated in FIG. 1, the introducer set 10 according to the present embodiment includes the introducer sheath 20 (corresponding to a medical elongated body) and the dilator 30 (corresponding to a medical instrument). The introducer sheath 20 and the dilator 30 will be described in detail below.

The introducer sheath 20 is placed into or positioned in a body lumen such as a blood vessel and forms an access path connecting the inside of a living body and the outside of the living body. For example, the introducer sheath 20 is used for inserting medical instruments such as a catheter and a guide wire through a lumen 111 of the introducer sheath 20 and inserting or introducing the medical instruments into a body lumen in a state where the introducer sheath 20 is placed or positioned in the body lumen. It is possible to perform a procedure such as percutaneous coronary intervention (PTCA/PCI) (hereinafter, referred to as "target procedure") by using the guide wire, the catheter, and the like inserted in the body lumen. Approach methods for the percutaneous coronary intervention include trans femoral intervention (TFI) for introducing the introducer sheath 20 from a foot blood vessel and trans radial intervention (TRI) for introducing the introducer sheath 20 from an arm blood vessel.

Figure 2:
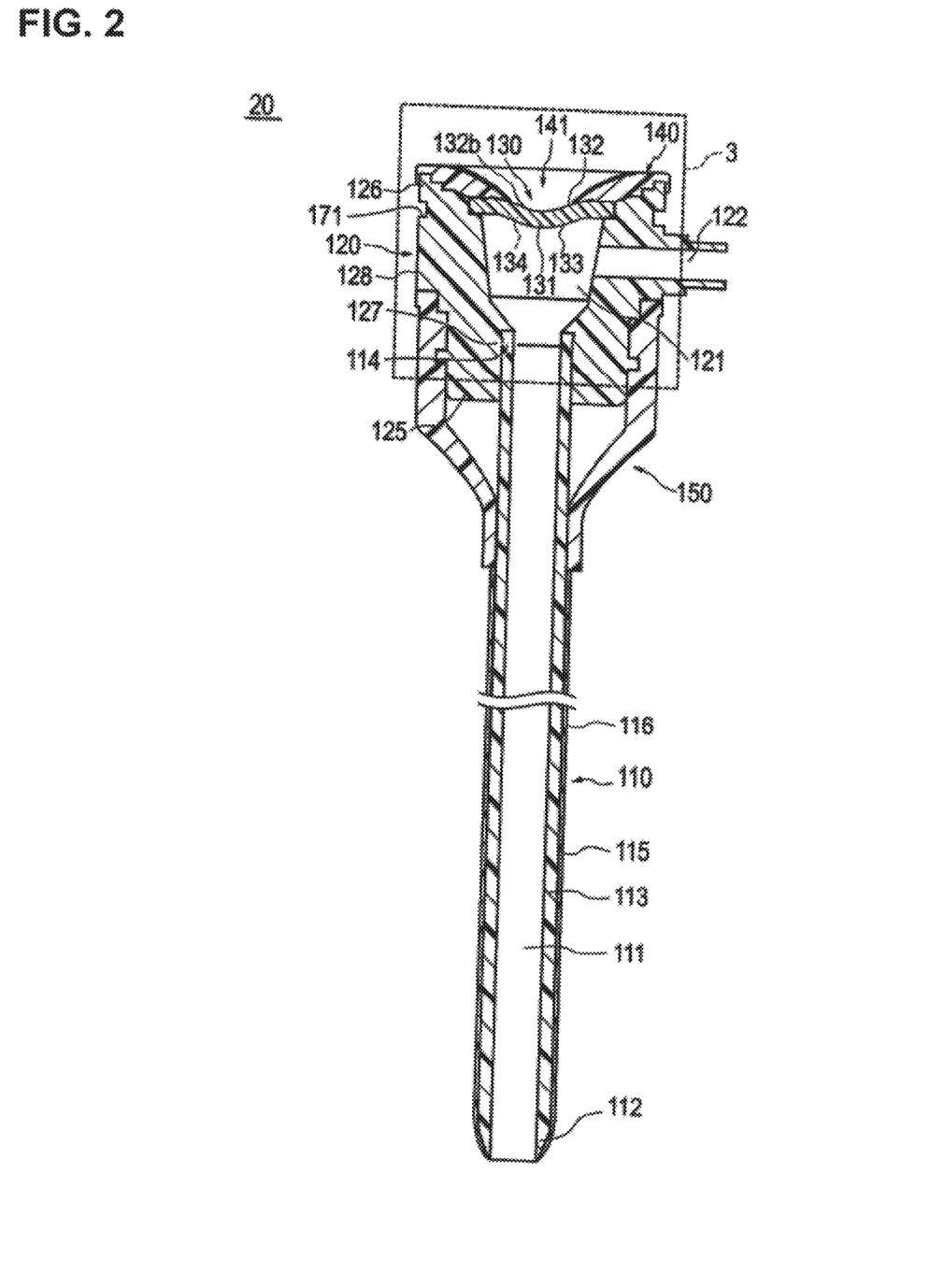
FIG. 2 is a cross-sectional view of an introducer sheath according to Embodiment 1.

Referring to FIG. 2, the introducer sheath 20 according to the present embodiment includes the catheter main body 110 (corresponding to a tubular body) insertable into a body lumen, the hub 120 having an internal space 121 communicating with the lumen 111 of the catheter main body 110 and disposed at a proximal portion 114 of the catheter main body 110, a hemostatic valve 130 (corresponding to a valve body) disposed in the internal space 121 and having an insertion portion 131, a cap 140 (corresponding to a cap member) fixing the hemostatic valve 130, and a strain relief 150 surrounding a predetermined range on the proximal side of the catheter main body 110.

Referring to FIG. 2, a substantially cylindrical tubular member having the lumen 111 constitutes the catheter main body 110. The catheter main body 110 has a tapered distal portion 112, a main body portion 113 located on the proximal side of the distal portion 112, and the proximal portion 114 located on the proximal side of the main body portion 113 and connected to the hub 120.

The constituent material from which the catheter main body 110 may be fabricated is not particularly limited. Examples of the constituent material include a polyolefin (such as polyethylene, polypropylene, polybutene, an ethylene-propylene copolymer, an ethylene-vinyl acetate copolymer, an ionomer, and a mixture of two or more of the materials), a polyolefin elastomer, a cross-linked polyolefin, polyvinyl chloride, a polyamide, a polyamide elastomer, a polyester, a polyester elastomer, polyurethane, a polyurethane elastomer, fluororesin, polycarbonate, polystyrene, polyacetal, polyimide, polyetherimide, an ethylene-tetrafluoroethylene copolymer (ETFE), a tetrafluoroethylene-hexafluoropropylene copolymer (FEP), polyether ether ketone (PEEK), polyvinylidene fluoride (PVDF), other polymer materials, and mixtures of the materials.

A hydrophilic lubricating layer 116, which provides surface lubricity when wet, is disposed on an outer surface 115 of the catheter main body 110.

The material that constitutes the hydrophilic lubricating layer 116 exhibits hydrophilicity and swelling when in contact with an aqueous solvent. The material that constitutes the hydrophilic lubricating layer 116 is not particularly limited insofar as the material exhibits hydrophilicity and swelling when in contact with an aqueous solvent. Known materials can be used as the material.

The hub 120 has the internal space 121 and a side port 122 communicating with the internal space 121.

The internal space 121 communicates with the lumen 111 of the catheter main body 110. The hemostatic valve 130 is disposed in the internal space 121.

One end of a flexible tube 71 (see FIG. 1) is connected in a liquid-tight manner to the side port 122. A three-way stopcock 72 is mounted at the other end of the tube 71. The side port 122 allows a liquid such as a physiological salt solution (saline solution) to be injected from the port of the three-way stopcock 72 into the lumen 111 of the catheter main body 110 via the tube 71. The tube 71 may be, for example, a known tube made of polyvinyl chloride.

The dilator hub 32 (described later) is fitted from the outside to the hub 120 (see FIG. 3). The hub 120 has an engagement groove 171, which engages with an engagement claw 172 of the dilator hub 32. The engagement groove 171 is shaped so as to be recessed from the outer surface 128 of the hub 120 toward the center side of the catheter main body 110. The engagement groove 171 is annularly formed along the circumferential direction of the catheter main body 110.

The constituent material from which the hub 120 may be fabricated is not particularly limited. A rigid material such as a rigid resin is suitable as the constituent material for the hub 120. Specific examples of the rigid resin include a polyolefin such as polyethylene and polypropylene, a polyamide, polycarbonate, and polystyrene.

The hemostatic valve 130 is disposed in the internal space 121 of the hub 120. The hemostatic valve 130 is attached to a proximal portion 126 of the hub 120. The hemostatic valve 130 has a substantially elliptical membrane shape (disk shape). The hemostatic valve 130 prevents the blood that has flowed into the catheter main body 110 from leaking to the outside.

The hemostatic valve 130 includes the insertion portion 131. The insertion portion 131 is configured to allow insertion of the dilator 30 and a medical instrument such as a catheter and a guide wire used for the target procedure.

The hemostatic valve 130 has a proximal surface 132 facing toward the proximal side of the catheter main body 110 and a distal surface 133 facing toward the distal side of the catheter main body 110.

The constituent material from which the hemostatic valve 130 may be fabricated is not particularly limited. Examples of the constituent material include silicone rubber, latex rubber, butyl rubber, and isoprene rubber as elastic members.

The proximal portion 114 of the catheter main body 110 is fixed to an interlock portion 127 of the hub 120. The proximal portion 114 of the catheter main body 110 and the interlock portion 127 of the hub 120 can be fixed by an adhesive or the like.

The cap 140 is attached to the hemostatic valve 130. The hemostatic valve 130 is fixed in the internal space 121 by being pinched between the hub 120 and the cap 140. For example, the cap 140 fixes the hemostatic valve 130 in the internal space 121 by being attached to the hemostatic valve 130 disposed in the concave portion of the hub 120 as illustrated in FIG. 2. The cap 140 has a proximal opening portion 141, which is capable of communicating with the internal space 121 via the insertion portion 131.

The strain relief 150 is externally fitted to the catheter main body 110 and the hub 120. The strain relief 150 covers a distal portion 125 of the hub 120 and surrounds a predetermined range on the proximal side of the catheter main body 110.

The constituent material from which the strain relief 150 may be fabricated is not particularly limited. Examples of the constituent material include natural rubber and silicone resins.

Next, the dilator 30 will be described with reference to FIGS. 1 and 3.

The dilator 30 includes a dilator main body 31 and the dilator hub 32, which is configured to be connectable to the hub 120.

The dilator main body 31 is insertable into the lumen 111 of the catheter main body 110. A substantially cylindrical tubular member having a lumen 31a constitutes the dilator main body 31. The lumen 31a is configured to allow insertion of a medical instrument such as a guide wire. A distal portion 31b of the dilator main body 31 is formed in a tapered shape and tapers in a narrowing manner toward the distal side.

The dilator hub 32 is connected to the hub 120 of the catheter main body 110 in a state where the dilator main body 31 is inserted or positioned in the lumen 111 of the catheter main body 110. The dilator hub 32 is fitted to the hub 120 of the catheter main body 110 from the outside of the catheter main body 110. The dilator hub 32 has the engagement claw 172, which engages the engagement groove 171 of the hub 120 of the catheter main body 110.

The distal portion 31b of the dilator main body 31 protrudes from the distal portion 112 of the catheter main body 110 in a state where the hub 120 of the introducer sheath 20 and the dilator hub 32 are connected to each other.

The introducer sheath 20 is inserted into a body lumen in the state of the introducer assembly in which the dilator main body 31 is positioned in the lumen 111 of the catheter main body 110 and the distal portion 31b of the dilator main body 31 protrudes from (i.e., distally beyond) the distal portion 112 of the catheter main body 110. As a result, the introducer sheath 20 is capable of widening a skin perforation with the distal portion 31b of the dilator main body 31 and preventing folding of the catheter main body 110 during introducer assembly insertion into a body lumen.

The material from which the dilator main body 31 may be fabricated is not particularly limited. Materials similar to conventionally used materials can be used for the dilator main body 31. Specific examples of the material include polyolefins such as polypropylene (PP) and polyethylene (PE), polyesters such as nylon and polyethylene terephthalate (PET), and fluorine-based polymers such as polyvinylidene fluoride (PVDF) and a tetrafluoroethylene-hexafluoropropylene copolymer (FEP).

The constituent material from which the dilator hub 32 may be fabricated is also not particularly limited. A rigid material such as a rigid resin is suitable for the dilator hub 32. Specific examples of the rigid resin include a polyolefin such as polyethylene and polypropylene, a polyamide, polycarbonate, and polystyrene.

Figure 4:
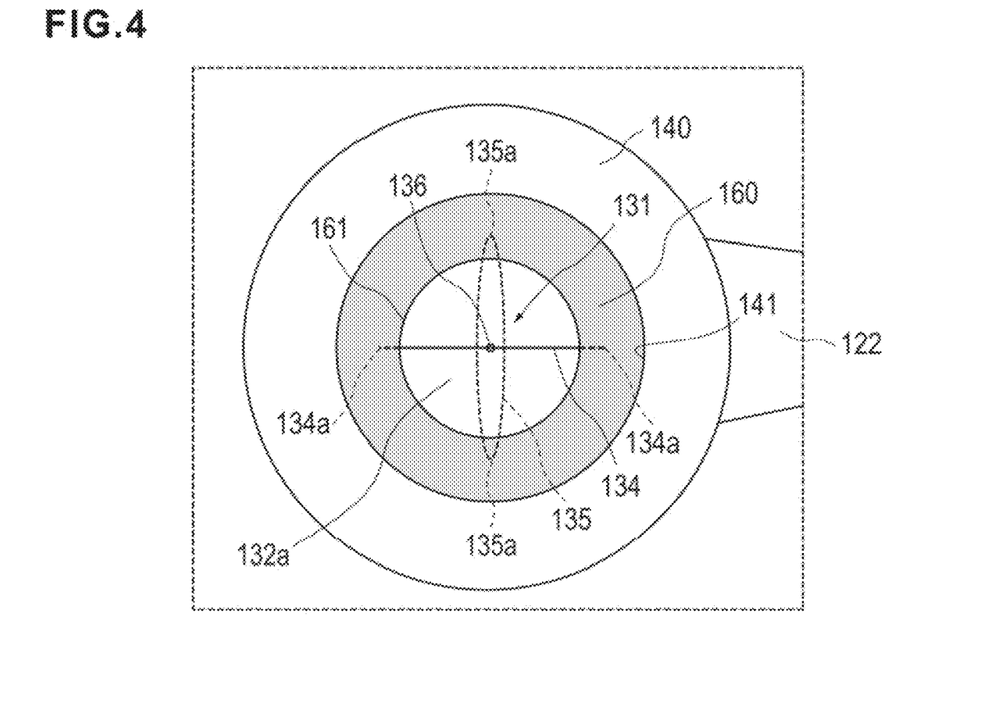
FIG. 4 is a plan view of the introducer sheath according to Embodiment 1.

Next, the hemostatic valve 130 and the cap 140 will be described in detail with reference to FIGS. 3 and 4.

The cap 140 has a marker portion 160, which guides a medical instrument inserted into the catheter main body 110 to the valve body. The marker portion 160 has a color that is color-perceptually distinguishable from the periphery of the marker portion 160. That is, there is a visually-observable color difference between the color of the marker portion 160 and the color of the portion of the cap 140 surrounding the marker portion 160. The color of the marker portion 160 is not particularly limited in terms of color type. The color of the marker portion 160 may be different from the color of the periphery the marker portion 160. It is preferable for marker portion visibility improvement that the color of the marker portion 160 is different from the color of the periphery of the marker portion 160 and the color of the hemostatic valve 130. For example, the marker portion 160 can be white in a case where the hemostatic valve 130 is colorless and transparent and the cap 140 is green. It is preferable that the hue difference between the colors of the marker portion 160 and the cap 140 is large (i.e., there is preferably a significant hue difference between the color of the marker portion 160 and color of the cap 140). The colors of the marker portion 160 and the cap 140 may be complementary to each other.

In inserting a medical instrument into the lumen 111 of the catheter main body 110 via the hemostatic valve 130, an operator can easily perform medical instrument centering toward the center side of the hemostatic valve 130 by visually recognizing the marker portion 160. The center side of the hemostatic valve 130 refers to the direction from the catheter main body 110 toward the insertion hole 136.

In plan view, the marker portion 160 may have a point-symmetrical shape with reference to the center portion of the hemostatic valve 130 in the radial direction of the catheter main body 110. For example, in FIG. 4, the center portion of the hemostatic valve 130 in the radial direction of the catheter main body 110 is the insertion hole 136. The marker portion 160 may have a ring shape or annular shape in plan view and may be spaced radially outwardly from the center of the valve body 130. In the present embodiment, a center side end portion 161 of the marker portion 160 forms the peripheral edge portion (inner peripheral edge) of the marker portion 160, and the center side end portion 161 of the marker portion 160 (i.e., the inner peripheral edge of the marker portion 160) is distal of the outer peripheral edge of the marker portion as shown in FIG. 3. The center side end portion 161 of the marker portion 160 is the place at which the inner periphery of the marker portion 160 intersects an axially outwardly facing surface of the hemostatic valve 130.

The marker portion 160 is disposed on the cap 140 so as to surround a surface 132a of the hemostatic valve 130 that is visually recognizable via the proximal opening portion 141. The surface 132a of the hemostatic valve 130 visually recognizable via the proximal opening portion 141 refers to the region that constitutes the proximal surface 132 of the hemostatic valve 130 and is visually recognizable from the proximal opening portion 141 in plan view of the introducer sheath 20.

The cap 140 has a guiding wall surface portion 142, which forms the proximal opening portion 141. The guiding wall surface portion 142 has a slope portion 143, which is inclined from the proximal side toward the distal side (inclined inwardly in a narrowing manner in the distal direction). The marker portion 160 is disposed on the slope portion 143.

The insertion portion 131 includes a proximal side slit 134 disposed in the proximal surface 132 and open to the proximal side and a distal side slit 135 disposed in the distal surface 133 and open to the distal side. The insertion portion 131 includes the insertion hole 136 at the place where the proximal side slit 134 and the distal side slit 135 intersect each other. A medical instrument is insertable into the lumen 111 of the catheter main body 110 via the insertion hole 136.

A curved surface directed from the proximal side toward the distal side constitutes the entire surface of the guiding wall surface portion 142. The center side end portion 161 (peripheral edge portion) of the marker portion 160 is disposed closer to the center side of the hemostatic valve 130 than end portions 134a and 135a of the slits 134 and 135 constituting the insertion portion 131. In other words, the end portions 134a and 135a of the slits 134 and 135 are positioned further radially outwardly than the center side end portion 161 (peripheral edge portion) of the marker portion 160 as shown in FIG. 4.

The center side end portion 161 (peripheral edge portion) of the marker portion 160 is in contact with the hemostatic valve 130. Specifically, the marker portion 160 disposed on the cap 140 is in contact with the hemostatic valve 130 by the cap 140 pressing the elastic hemostatic valve 130. In addition, the marker portion 160 disposed on the cap 140 is disposed so as to cover a projection portion 144 (described later), and thus the marker portion 160 disposed on the cap 140 comes into contact with the hemostatic valve 130 when the cap 140 is attached to the hemostatic valve 130.

The cap 140 has the projection portion 144, which protrudes toward the hemostatic valve 130 and presses the center of the hemostatic valve 130 so as to be concave to the distal side. The proximal surface 132 of the hemostatic valve 130 includes a curved surface 132b, which is concavely curved by the projection portion 144. The curved surface of the guiding wall surface portion 142 is smoothly continuous with the curved surface 132b.

Referring to FIG. 1, the distal portion 31b of the dilator 30 is provided with a distal end marker portion 33, which has a color that is color-perceptually distinguishable (i.e., a color that is visually distinguishable) from the surrounding. The distal end marker portion 33 can be red in a case where, for example, the dilator main body 31 is blue.

In the introducer sheath 20 according to the present embodiment, the cap 140 has the marker portion 160, which guides a medical instrument inserted into the catheter main body 110 to the hemostatic valve 130. The marker portion 160 has a color distinguishable (visually distinguishable) from the periphery or surrounding portion of the marker portion 160. As a result, in inserting a medical instrument (such as the dilator 30 and a catheter and a guide wire used for the target procedure) into the lumen 111 of the catheter main body 110 via the hemostatic valve 130, an operator can easily grasp the position of the hemostatic valve 130 by visually recognizing the marker portion 160. Accordingly, the operator can easily guide the distal portion of the medical instrument to the vicinity of the center of the hemostatic valve 130 by aiming at the position indicated by the marker portion 160. Accordingly, it is possible to provide an introducer sheath having a simple structure that allows quick insertion of a medical instrument into a catheter main body lumen via a hemostatic valve.

In addition, the following is possible as the operator can easily guide the distal portion of the medical instrument to the vicinity of the center of the hemostatic valve 130. In other words, contact between the most distal end of the medical instrument and a place other than the hemostatic valve 130 can be suppressed or reduced when the operator inserts the medical instrument into the lumen 111 of the catheter main body 110 via the hemostatic valve 130. Accordingly, it is possible to inhibit damage to the distal portion of the medical instrument attributable to contact with a place other than the hemostatic valve 130.

In forming or assembling the introducer assembly in particular, the operator can easily inhibit damage to the dilator 30 attributable to contact between the distal portion 31b of the dilator 30 and a place other than the hemostatic valve 130 by aligning the distal portion 31b of the dilator 30 in the marker portion 160. In addition, it is possible to reduce the necessity for the operator to pay attention such that the dilator 30 does not come into contact with a place other than the hemostatic valve 130 during the formation of the introducer assembly, and thus the procedure can be performed in a labor-saving manner and the operator can concentrate on the procedure.

In the introducer sheath 20 according to the present embodiment, the marker portion 160 is disposed on the cap 140 so as to surround the surface 132a of the hemostatic valve 130 that is visually recognizable via the proximal opening portion 141. As a result, the operator can more easily grasp the position of the hemostatic valve 130 by visually recognizing the marker portion 160 on the hand-side of the introducer sheath 20. Accordingly, the operator can more easily guide the distal portion of the medical instrument to the vicinity of the center of the hemostatic valve 130.

In the introducer sheath 20 according to the present embodiment, the marker portion 160 is disposed on the slope portion 143 of the guiding wall surface portion 142. As a result, the distal portion of the medical instrument comes into contact with the slope portion 143 even in the event of deviation of the distal portion of the medical instrument from the vicinity of the center of the hemostatic valve 130 to the marker portion 160 side. The distal portion of the medical instrument that is in contact with the slope portion 143 is guided to the hemostatic valve 130 along the slope portion 143, and thus damage to the medical instrument can be inhibited. Accordingly, the necessity for the operator to pay attention such that the distal portion of the medical instrument does not come into contact with a place other than the hemostatic valve 130 is reduced. As a result, it is possible to further expedite medical instrument insertion into the lumen 111 of the catheter main body 110 via the hemostatic valve 130.

The slope portion 143 inclined toward the hemostatic valve 130 is easily visible in plan view. Accordingly, the operator can easily grasp the position of the marker portion 160 and the medical instrument and the marker portion 160 are aligned with ease.

In the introducer sheath 20 according to the present embodiment, the center side end portion 161 of the marker portion 160 is disposed closer to the center side of the hemostatic valve 130 than the end portions 134a and 135a of the slits 134 and 135 constituting the insertion portion 131. That is, that the center side end portion 161 of the marker portion 160 is disposed inwardly (radially inwardly) of the end portions 134a, 135a of the slits 134, 135. As a result, damage to the insertion portion 131 of the hemostatic valve 130 attributable to contact of the distal portion of the medical instrument with the end portions 134a and 135a of the slits 134 and 135 can be inhibited by the operator aligning the medical instrument and the marker portion 160 in inserting the medical instrument into the lumen 111 of the catheter main body 110 via the hemostatic valve 130.

In forming or assembling the introducer assembly in particular, the operator can easily grasp the positions of the slits 134 and 135 by using the marker portion 160 as a mark. Accordingly, it is possible to easily inhibit damage to the hemostatic valve 130 attributable to contact between the distal portion 31b of the dilator 30 and a place other than the insertion portion 131 of the hemostatic valve 130.

A curved surface directed from the proximal side toward the distal side constitutes the entire surface of the guiding wall surface portion 142. Accordingly, damage to the medical instrument can be inhibited even in the event of contact between the medical instrument and the guiding wall surface portion 142.

In the introducer sheath 20 according to the present embodiment, the center side end portion 161 of the marker portion 160 is in contact with the hemostatic valve 130. As a result, the operator can more clearly distinguish the boundary between the hemostatic valve 130 and the part other than the hemostatic valve 130 by visually recognizing the marker portion 160. Accordingly, the operator can more easily guide the distal portion of the medical instrument to the vicinity of the center of the hemostatic valve 130 by aiming at the position indicated by the marker portion 160.

In the set of the introducer sheath 20 and the dilator 30 according to the present embodiment, the medical elongated body is the introducer sheath 20 and the distal portion 31b of the dilator 30 is provided with the distal end marker portion 33, which has a color distinguishable from the surrounding. As a result, the operator can more easily guide the distal portion 31b of the dilator 30 to the vicinity of the center of the hemostatic valve 130 by aligning the marker portion 160 of the introducer sheath 20 and the distal end marker portion 33 of the dilator 30 in forming the introducer assembly by inserting the dilator 30 into the lumen 111 of the catheter main body 110.

In the introducer sheath according to the present embodiment, the cap 140 has the projection portion 144, which protrudes toward the hemostatic valve 130 and presses the center of the hemostatic valve 130 so as to be concave to the distal side. The proximal surface 132 of the hemostatic valve 130 includes the curved surface 132b, which is concavely curved by the projection portion 144. The curved surface of the guiding wall surface portion 142 is smoothly continuous with the curved surface 132b. As a result, the medical instrument is guided by the curved surface 132b smoothly continuous from the guiding wall surface portion 142 and guided to the middle portion of the hemostatic valve 130, which has a small resistance force at a time of insertion, even in the case of contact with a place other than the insertion portion 131 of the hemostatic valve 130 or the guiding wall surface portion 142. Accordingly, injuries to the medical instrument and the hemostatic valve 130 can be inhibited.

Modification Example 1

In the embodiment described above, the dilator 30 is fitted to the outside of the introducer sheath 20. Alternatively, the dilator 30 may be fitted to the inside of the introducer sheath 20.

Figure 5:
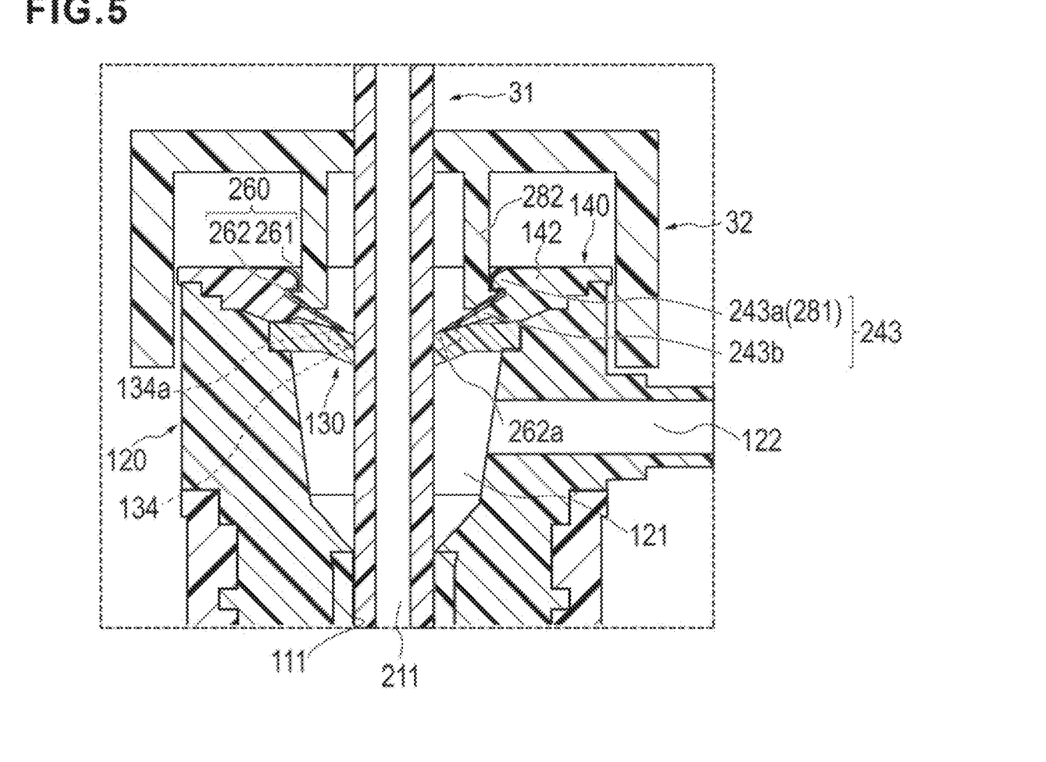
FIG. 5 is an enlarged view corresponding to FIG. 3 and illustrating an introducer set according to Modification Example 1 of Embodiment 1.
Figure 6:
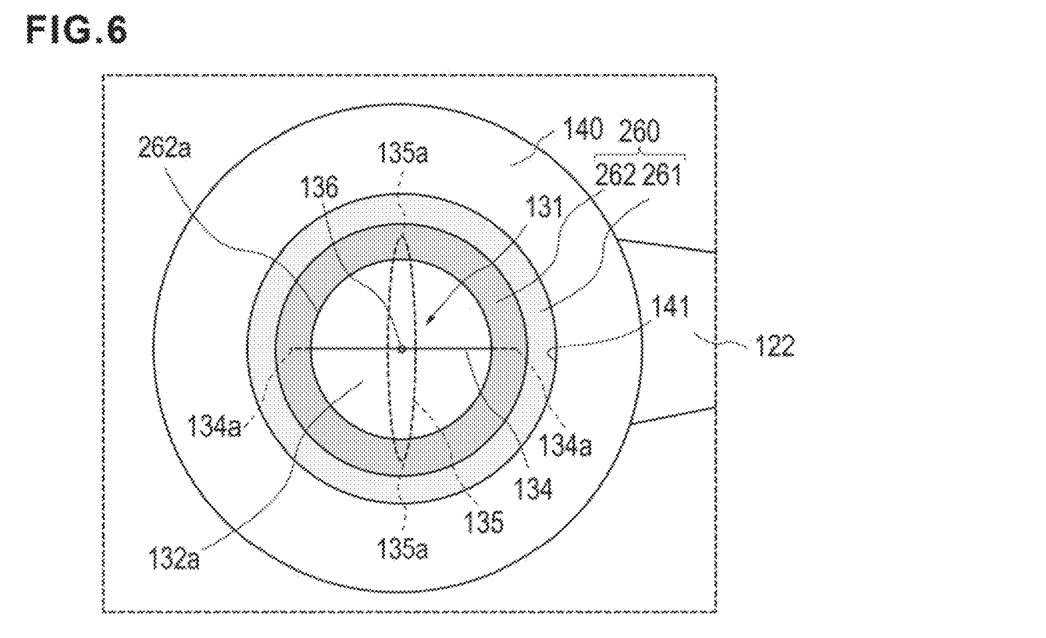
FIG. 6 is a plan view of an introducer sheath according to Modification Example 1 of Embodiment 1.

FIG. 5, which corresponds to FIG. 3, is an enlarged view illustrating an introducer set according to the present modification example. FIG. 6 is a plan view of an introducer sheath according to the present modification example.

In the introducer set according to the present modification example, the cap 140 has an engagement claw 281, which engages with an engagement claw 282 of the dilator hub 32. The engagement claw 281 protrudes toward the center side of the catheter main body 110 in the proximal opening portion 141 of the cap 140.

The dilator hub 32 has the engagement claw 282, which engages with the engagement claw 281 of the cap 140. The engagement claw 282 protrudes from a surface of the dilator hub 32 that faces the distal side and extends along the axial direction.

The guiding wall surface portion 142 has a slope portion 243, which forms the proximal opening portion 141. The slope portion 243 has a first slope portion 243a and a second slope portion 243b, which is formed closer to the distal side than the first slope portion 243a. The first slope portion 243a functions as the engagement claw 281 of the introducer sheath 20. The second slope portion 243b protrudes to the center side of the catheter main body 110 beyond the first slope portion 243a.

A marker portion 260 has a first marker portion 261 disposed on the first slope portion 243a and a second marker portion 262 disposed on the second slope portion 243b.

Although the colors of the first marker portion 261 and the second marker portion 262 are color-perceptually distinguishable from each other, the first marker portion 261 and the second marker portion 262 may have the same color. For example, the first marker portion 261 can be black and the second marker portion 262 can be white.

The first marker portion 261 and the second marker portion 262 are disposed so as to surround the surface 132a of the hemostatic valve 130 that is visually recognizable via the proximal opening portion 141. The first marker portion 261 and the second marker portion 262 have a ring shape or annular shape in plan view. In the present modification example, a center side end portion 262a of the second marker portion 262 forms the peripheral edge portion of the marker portion 260 that is on the distal side along the circumferential direction of the catheter main body 110.

The center side end portion 262a (peripheral edge portion) of the second marker portion 262 is disposed closer to the center side of the hemostatic valve 130 than the end portions 134a and 135a of the slits 134 and 135 constituting the insertion portion 131. In other words, the end portions 134a and 135a of the slits 134 and 135 are positioned further radially outwardly than the center side end portion 262a of the second marker portion 262.

The center side end portion 262a (peripheral edge portion) of the second marker portion 262 is in contact with the hemostatic valve 130.

The present modification example is similar in action and effect to the introducer set 10 according to the embodiment described above.

Modification Example 2

The marker portion may be comprised of a plurality of colors.

Figure 7:
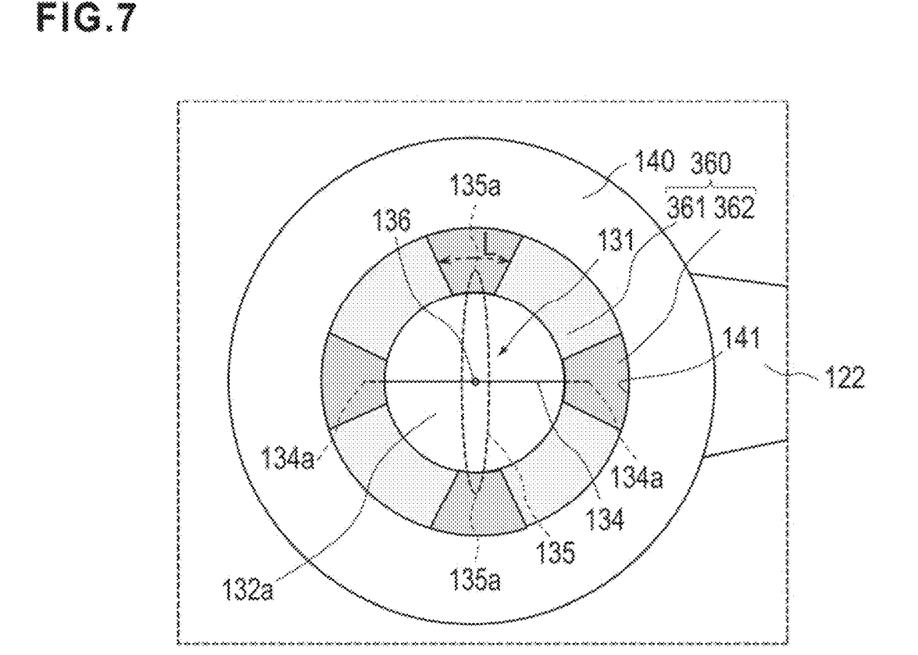
FIG. 7 is a plan view of an introducer sheath according to Modification Example 2 of Embodiment 1.

FIG. 7 is a plan view of an introducer sheath according to such a modification example.

A marker portion 360 of the introducer sheath according to the present modification example includes a first region 361 and a second region 362, which is different in color from the first region 361. In the illustrated embodiment, several of the first regions 361 and several of the second regions 362 are provided, with the first regions 361 and the second regions 362 circumferentially alternating with one another as depicted by way of example in FIG. 7.

The overall configuration of the marker portion 360 is the same as the overall configuration of the marker portion 160 according to the above-described embodiment, except that the marker portion 360 depicted in the FIG. 7 embodiment is defined by the circumferentially alternating first and second regions 361, 362.

Each of the second regions 362 is disposed at a predetermined position between two of the first regions 361, and the first regions 361 and the second regions 362 are located at a radially outward portion of the hemostatic valve 130. A width L of the second region 362 decreases from the outer periphery of the cap 140 toward the hemostatic valve 130. In this specification, "width" means the length of the second region 362 along the circumferential direction of the catheter main body 110.

With the introducer sheath according to the present modification example, the visibility of the marker portion 360 is improved. Accordingly, the distal portion of a medical instrument can be more easily guided to the vicinity of the center of the hemostatic valve 130 by a simple structure, that is, by the marker portion 360 being provided.

The colors that constitute the marker portion 360 are not limited to the two colors described above. Alternatively, three or more colors may constitute the marker portion 360.

The first marker portion 261 and/or the second marker portion 262 of Modification Example 1 described above may be similar in configuration to the marker portion 360 according to the present modification example.

Embodiment 2

In the embodiment and the modification examples described above, the marker portion 160 is provided on the cap 140. Alternatively, a marker portion may be provided on the hemostatic valve 130.

An introducer set according to the present embodiment is similar in configuration to the introducer sets according to the above-described embodiment and modification examples except for the configuration of the marker portion. Accordingly, only the marker portion will be described below.

Figure 8:
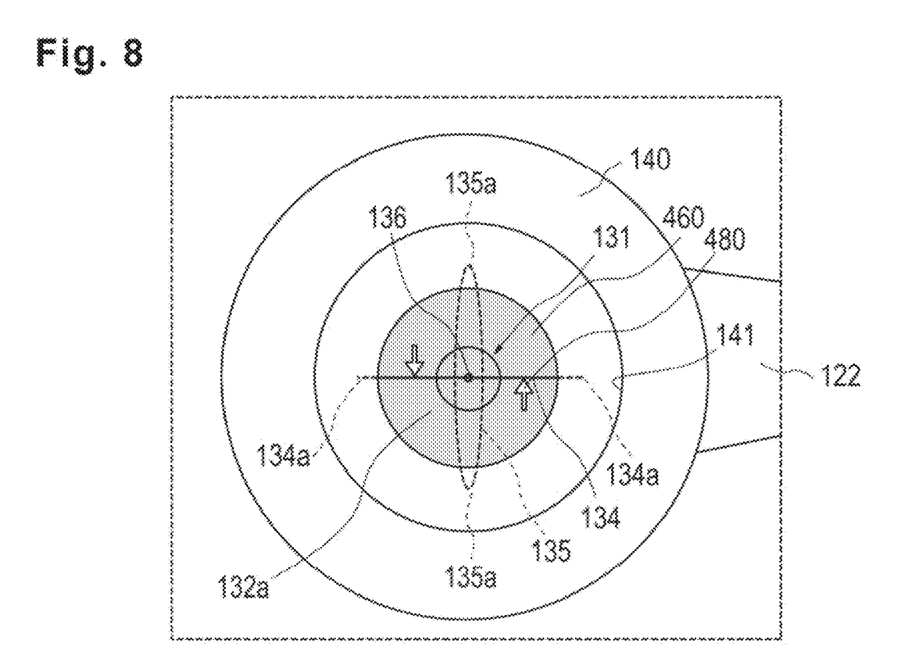
FIG. 8 is a plan view of an introducer sheath according to Embodiment 2.

FIG. 8 is a plan view of an introducer sheath according to the present embodiment.

Referring to FIG. 8, the hemostatic valve 130 has a marker portion 460, which guides a medical instrument inserted into catheter main body 110 to the insertion portion 131.

The marker portion 460 has a color that is color-perceptually distinguishable from the periphery of the marker portion 460. That is, the color of the marker portion 460 is visually distinguishable from the color of the periphery of the marker portion 460. The marker portion 460 is not particularly limited in terms of color type. For example, the marker portion 160 can be white in a case where the hemostatic valve 130 is colorless and transparent and the cap 140 is green. As illustrated in FIG. 8, the marker portion 460 may be a circular or disk-shaped marker portion.

The marker portion 460 is provided so as to surround the insertion hole 136 of the hemostatic valve 130 on the curved surface 132b (see FIG. 2) of the hemostatic valve 130.

The introducer sheath may also include a slit distinguishing portion 480 that makes the proximal side slit 134 and the distal side slit 135 distinguishable from each other.

The slit distinguishing portion 480 indicates the position of the proximal side slit 134. In the illustrated embodiment, the slit distinguishing portion 480 is positioned on the proximal facing surface of the valve body 130 and may be configured as an arrow shape indicating the position of the proximal side slit 134. In the illustrated embodiment, the distal surface of the valve body 13 may be devoid of any slit distinguishing portions. The slit distinguishing portion 480 is disposed in the marker portion 460. The slit distinguishing portion 480 may be of a color that is color-perceptually distinguishable from the marker portion 460. That is, the color of the slit distinguishing portion 480 is visually distinguishable from the color of the marker portion 460.

The introducer sheath according to the present embodiment has the following actions and effects in addition to the actions and effects of the introducer sheath 20 according to the above-described embodiment.

In other words, with the introducer sheath according to the present embodiment, an operator can easily grasp the position of the insertion portion 131 of the hemostatic valve 130 by visually recognizing the position of the marker portion 460 in inserting a medical instrument into the lumen 111 of the catheter main body 110 via the hemostatic valve 130. Accordingly, it is possible to easily inhibit damage to the hemostatic valve 130 attributable to contact between the distal portion of the medical instrument and a place other than the insertion portion 131 of the hemostatic valve 130 when the operator inserts the medical instrument into the lumen 111 of the catheter main body 110 via the hemostatic valve 130.

In the introducer sheath according to the present embodiment, the marker portion 460 is provided so as to surround the insertion hole 136. Accordingly, it is possible to prevent contact between the distal portion of the medical instrument and a place other than the insertion hole 136 when the operator inserts the medical instrument into the lumen 111 of the catheter main body 110 via the hemostatic valve 130. Accordingly, damage to the hemostatic valve 130 can be easily and more reliably inhibited.

The distal side slit 135 is provided in the distal surface 133 of the hemostatic valve 130 and is open to the distal side. Accordingly, the risk of the hemostatic valve 130 being injured by the distal portion of the medical instrument is high in a case where the medical instrument is moved in toward the distal side slit 135 instead of the insertion hole 136. The proximal side slit 134 is provided in the proximal surface 132 of the hemostatic valve 130 and is open to the proximal side. Accordingly, the operator can insert the medical instrument through the insertion hole 136 while inhibiting or avoiding damage to the hemostatic valve 130, by moving the distal portion of the medical instrument along the proximal side slit 134, even with the medical instrument moved in toward the proximal side slit 134 instead of the insertion hole 136.

With the introducer sheath according to the present embodiment, it is possible to distinguish the proximal side slit 134 and the distal side slit 135 from each other by visually recognizing the slit distinguishing portion 480. Accordingly, it is possible to reduce the risk that the operator erroneously moves the medical instrument into the distal side slit 135 when the operator inserts the medical instrument into the lumen of the catheter main body via the hemostatic valve. As a result, it is possible to provide an introducer sheath having a simple structure that allows more reliable prevention of damage to the hemostatic valve 130 during insertion of the medical instrument into the lumen 111 of the catheter main body 110 via the hemostatic valve 130.

Modification Example

The marker portion may have a plurality of colors.

Figure 9:
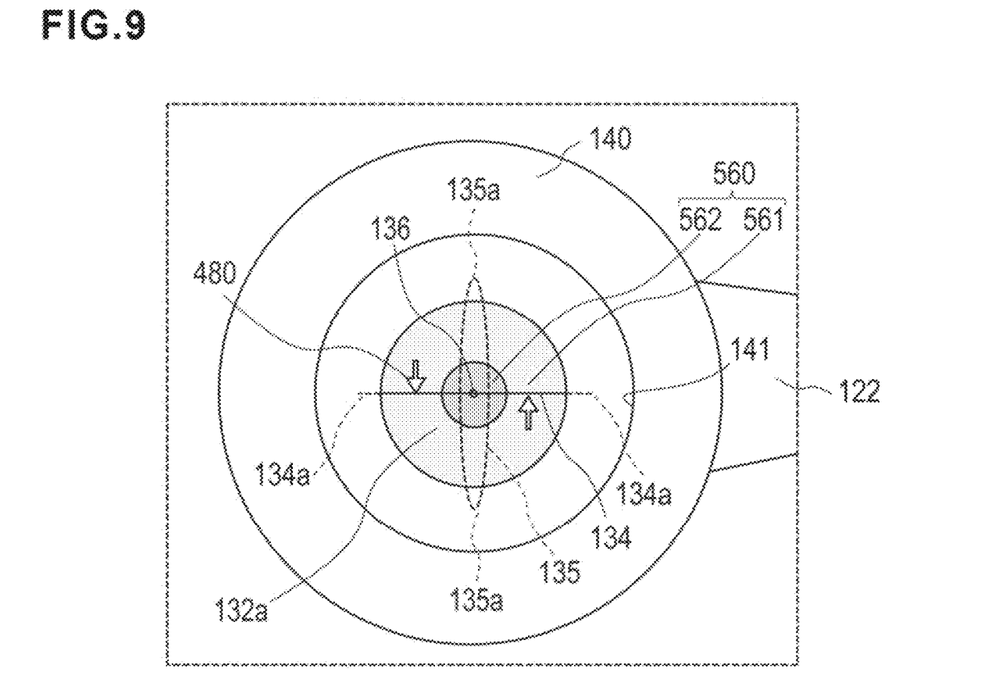
FIG. 9 is a plan view of an introducer sheath according to a modification example of Embodiment 2.

FIG. 9 is a plan view of an introducer sheath according to the present modification example.

A marker portion 560 according to the present modification example includes a first region 561 and a second region 562, which is different in color from the first region 561. The configuration of the first region 561 is the same as the configuration of the marker portion 460 according to Embodiment 2 described above. The second region 562 is disposed closer to the center side of the introducer sheath 20 (center side of the hemostatic valve 130) than the first region 561. The second region 562 has a circular shape about the insertion hole 136. The second region 562 can be, for example, red.

Although FIG. 9 exemplifies a case where the marker portion has two colors, the colors that constitute the marker portion are not limited to the two colors described above and three or more colors may constitute the marker portion. It is possible to improve the visibility of the marker portion by changing the shape of the marker portion or the colors constituting the marker portion and the combination of the colors.

Although an introducer sheath has been described above based on embodiments and modification examples, the invention is not limited to the configurations described in the embodiments and the modification examples. The invention can be appropriately changed based on the claims.

In the above-described embodiments and modification examples, the marker portion is provided on either the hemostatic valve 130 or the cap 140. Alternatively, the marker portion may be provided on both the hemostatic valve 130 and the cap 140.

In Embodiment 2 described above, the form of the slit distinguishing portion 480 is a form that has an arrow shape indicating the position of the proximal side slit 134. However, the slit distinguishing portion 480 may have any form as long as it can make the proximal side slit 134 and the distal side slit 135 distinguishable from each other. For example, the form may be a triangular or rhombic shape that indicates the position of the proximal side slit 134. In the marker portion 460, a belt-shaped site having a color that is color-perceptually distinguishable from the surrounding may be formed along the proximal side slit 134 and the site may be used as the slit distinguishing portion 480. In addition, the slit distinguishing portion 480 may be provided on the cap 140. Further, the hemostatic valve 130 and/or the cap 140 of the introducer sheaths according to Embodiment 1 and the modification examples of Embodiment 1 may also be provided with the slit distinguishing portion.

The dilator is connected to the hub of the catheter main body in Embodiment 1, Modification Example 2 of Embodiment 1, Embodiment 2, and the modification example of Embodiment 2. Alternatively, the dilator may be configured to be connected to the cap. Methods for connecting the dilator and the cap to each other are not particularly limited. The dilator and the cap can be connected to each other by, for example, a method of forming an engagement claw on the cap as in Modification Example 1 of Embodiment 1.

The detailed description above describes embodiments of a medical elongated body and a medical elongated body set representing examples of the inventive medical elongated body and a medical elongated body set disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical elongated body comprising:
a tubular body insertable into a body lumen of a patient, the tubular body including a lumen;
a hub that includes an internal space communicating with the lumen of the tubular body and disposed in a proximal portion of the tubular body;
a valve body disposed in the internal space of the hub and including an insertion portion through which is insertable a medical instrument when the tubular body is positioned in the body lumen of the patient to introduce the medical instrument into the body lumen of the patient;
a cap member attached to the valve body in a manner fixing the valve body in the internal space of the hub, the cap member including a proximal opening portion configured to communicate with the internal space via the insertion portion;
the cap member including a marker portion that guides the medical instrument to the valve body during insertion of the medical instrument into the tubular body; and
the marker portion being of a color that is visually distinguishable from a periphery of the marker portion.

2. The medical elongated body according to claim 1, wherein the marker portion is disposed on the cap member and surrounds a surface of the valve body that is visually recognizable while viewing the proximal opening portion.

3. The medical elongated body according to claim 1, wherein
the cap member possesses a guiding wall surface portion forming the proximal opening portion,
the guiding wall surface portion including a slope portion that is inclined from a proximal side of the tubular body toward a distal side of the tubular body, and
the marker portion is disposed on the slope portion of the guiding wall surface portion.

4. The medical elongated body according to claim 3, wherein
the guiding wall surface portion of the cap member is constituted by a curved surface directed from a proximal side of the tubular body toward a distal side of the tubular body, the curved surface constituting an entirety of the surface of the guiding wall surface portion,
the insertion portion is comprised of a slit in the valve body; and
a center side end portion of the marker portion is disposed closer to a center of the valve body than a radially outer end portion of the slit in the valve body.

5. The medical elongated body according to claim 1, wherein
the marker portion includes a first region and a second region, the second region being different in color from the first region,
the second region is disposed in a radiation direction of the valve body at a predetermined position of the first region, and
the second region decreases in width from an outer portion of the second region toward an inner portion of the second region.

6. The medical elongated body according to claim 1, wherein a center side end portion of the marker portion is in contact with the valve body.

7. A medical elongated body comprising:
a tubular body insertable into a body lumen of a patient, the tubular body including a lumen;
a hub that includes an internal space communicating with the lumen of the tubular body and disposed in a proximal portion of the tubular body;
a valve body disposed in the internal space of the hub and including an insertion portion through which is insertable a medical instrument when the tubular body is positioned in the body lumen of the patient to introduce the medical instrument into the body lumen of the patient;
a cap member attached to the valve body in a manner fixing the valve body in the internal space of the hub, the cap member including a proximal opening portion configured to communicate with the internal space via the insertion portion;
the valve body including a marker portion that guides the medical instrument to the insertion portion during insertion of the medical instrument into the tubular body, and
the marker portion being of a color that is visually distinguishable from a periphery of the marker portion.

8. The medical elongated body according to claim 7, wherein
the valve body possesses a distal surface facing the internal space and a proximal surface facing away from the internal space,
the insertion portion includes a proximal side slit provided in the proximal surface of the valve body and open to the proximal surface, a distal side slit provided in the distal surface of the valve body and open to the distal surface, and an insertion hole located at a place where the proximal side slit and the distal side slit intersect each other,
the medical elongated body further comprising a slit distinguishing portion that distinguishes the proximal side slit and the distal side slit from each other.

9. The medical elongated body according to claim 8, wherein the marker portion surrounds the insertion hole of the valve body.

10. The medical elongated body according to claim 7, wherein the valve body includes a proximal surface facing away from the internal space, the proximal surface being a curved surface, the marker portion being located on the curved surface of the valve body.

11. The medical elongated body according to claim 7, wherein the marker portion surrounds the insertion portion of the valve body.

12. The medical elongated body according to claim 7, wherein the marker portion is a disk-shaped marker portion.

13. The medical elongated body according to claim 7, wherein the valve body includes a proximal side slit and a distal side slit on opposite surfaces of the valve body, the marker portion that is of a color that is visually distinguishable from the periphery of the marker portion possessing an outermost periphery, the proximal side slit and the distal side slit including outermost portions that extend radially outwardly beyond the outermost periphery of the marker portion.

14. A medical elongated body set comprising:
a medical elongated body according to claim 7; and
a dilator insertable into a lumen of the medical elongated body, the dilator including a distal portion;
the medical elongated body being an introducer sheath, and the distal end portion of the dilator including a distal end marker portion that is color distinguishable from an immediately adjacent part of the dilator.

15. A medical elongated body comprising:
a tubular body possessing a lumen into which a medical instrument is insertable, the tubular body possessing a proximal portion;
a hub connected to the proximal portion of the tubular body, the hub possessing an internal space communicating with the lumen of the tubular body, the hub also possessing an inner surface and a proximal portion;
a valve body disposed in the proximal portion of the hub and covering the internal space so that the internal space is bounded by the valve body and the inner surface of the hub, the valve body possessing a center and including an insertion portion into which the medical instrument is insertable, the valve body possessing a proximal surface facing away from the tubular body and a distal surface facing toward the tubular body;
the valve body including a proximal surface and a distal surface positioned on opposite surfaces of the valve body;
a cap member attached to the proximal portion of the hub and being in direct contact with the proximal surface of the valve body, the cap member possessing a centrally located proximal opening portion passing through the cap member, the insertion portion being exposed in the proximal opening portion of the cap member so that the medical instrument is insertable into the insertion portion of the valve body while passing through the proximal opening portion of the cap member;
the cap member including a marker portion that guides the medical instrument to the insertion portion of the valve body during insertion of the medical instrument into the tubular body, the marker portion including an inner periphery and an outer periphery, the marker portion between the inner periphery and the outer periphery being visually distinguishable from an adjacent portion of the cap member that is immediately adjacent the marker portion;
the insertion portion including a proximal side slit located on the proximal surface of the valve body and a distal side slit located on the distal surface of the valve body, the proximal side slit including oppositely disposed end portions, the distal side slit intersecting the proximal side slit;
the cap member being in direct contact with the proximal surface of the valve body at a position that is closer to the center of the valve body than both end portions of the proximal side slit of the valve body; and
the marker portion being disposed at a position surrounding the proximal side slit while covering both end portions of the proximal side slit.

16. The medical elongated body according to claim 15, wherein the marker portion is a ring-shaped marker portion and is spaced radially outwardly from a center of the valve body as seen from a proximal end of the cap member.

17. The medical elongated body according to claim 15, wherein the marker portion is a ring-shaped marker portion comprised of a first region and a second region, the first region being of a color different form the second region.

18. The medical elongated body according to claim 17, wherein the first region and the second region are positioned circumferentially adjacent one another, the first region and the second region both possessing a varying width in a radial direction.

19. The medical elongated body according to claim 15, wherein the marker portion is a ring-shaped marker portion comprised of first regions and second regions that circumferentially alternate with one another, the first regions being of a color different form the second regions.

20. The medical elongated body according to claim 15, wherein the cap member possesses a proximally facing guiding wall surface that faces away from the internal space, the guiding wall surface being inclined from a proximal side of the tubular body toward a distal side of the tubular body, and the marker portion being disposed on the inclined guiding wall surface.

21. The medical elongated body according to claim 15, wherein the marker portion between the inner periphery and the outer periphery is color distinguishable from the adjacent portion that is immediately adjacent the marker portion.

22. A medical elongated body comprising:
a tubular body possessing a lumen into which a medical instrument is insertable, the tubular body possessing a proximal portion;
a hub connected to the proximal portion of the tubular body, the hub possessing an internal space communicating with the lumen of the tubular body, the hub also possessing an inner surface and a proximal portion;
a valve body disposed in the proximal portion of the hub and covering the internal space so that the internal space is bounded by the valve body and the inner surface of the hub, the valve body possessing a center and including an insertion portion into which the medical instrument is insertable, the valve body possessing a proximal surface facing away from the tubular body and a distal surface facing toward the tubular body;
the valve body including a proximal surface and a distal surface positioned on opposite surfaces of the valve body;
a cap member attached to the proximal portion of the hub and being in direct contact with the proximal surface of the valve body, the cap member possessing a centrally located proximal opening portion passing through the cap member, the insertion portion being exposed in the proximal opening portion of the cap member so that the medical instrument is insertable into the insertion portion of the valve body while passing through the proximal opening portion of the cap member;
the cap member including a marker portion that guides the medical instrument to the insertion portion of the valve body during insertion of the medical instrument into the tubular body, the marker portion including an inner periphery and an outer periphery, the marker portion between the inner periphery and the outer periphery being color distinguishable from an adjacent portion that is immediately adjacent the marker portion;
the insertion portion including a proximal side slit located on the proximal surface of the valve body and a distal side slit located on the distal surface of the valve body, the proximal side slit including oppositely disposed end portions, the distal side slit intersecting the proximal side slit;
the cap member being in direct contact with the proximal surface of the valve body at a position that is closer to the center of the valve body than both end portions of the proximal side slit of the valve body; and
the marker portion being disposed at a position surrounding the proximal side slit while covering both end portions of the proximal side slit.

\* \* \* \* \*